(12) United States Patent
Scholz et al.

(10) Patent No.: US 8,155,732 B2
(45) Date of Patent: Apr. 10, 2012

(54) ECG SYSTEM FOR USE IN ECG SIGNAL MEASUREMENT OF INTRA-CARDIAC ECG USING A CATHETER

(75) Inventors: Wolfgang Scholz, Beverly, MA (US); Clifford Risher-Kelly, Wells, ME (US)

(73) Assignee: Draeger Medical Systems, Inc., Andover, MA (US)

( * ) Notice: Subject to any disclaimer, the term of this patent is extended or adjusted under 35 U.S.C. 154(b) by 333 days.

(21) Appl. No.: 12/447,719

(22) PCT Filed: Nov. 9, 2007

(86) PCT No.: PCT/US2007/084272
§ 371 (c)(1),
(2), (4) Date: Apr. 29, 2009

(87) PCT Pub. No.: WO2008/061010
PCT Pub. Date: May 22, 2008

(65) Prior Publication Data
US 2010/0004547 A1 Jan. 7, 2010

(51) Int. Cl.
A61B 5/04 (2006.01)
(52) U.S. Cl. ...................................................... 600/509
(58) Field of Classification Search .................. 600/509, 600/374; 607/119
See application file for complete search history.

(56) References Cited

U.S. PATENT DOCUMENTS

| 4,742,831 A | * | 5/1988 | Silvian ........................ 600/523 |
| 5,666,958 A | | 9/1997 | Rothenberg et al. |
| 5,743,859 A | | 4/1998 | Wodlinger et al. |
| 6,324,416 B1 | | 11/2001 | Seibert |

FOREIGN PATENT DOCUMENTS

EP 0 835 635 4/1998

OTHER PUBLICATIONS

"Central Venous Catheter Placement in Hemodialysis: Evaluation of Electrocardiography Using a Guide Wire", The Journal of Vascular Access, 2001, pp. 45-50, Cavatorta et al.
"Getting the Most From a CVP Catheter", Atlas of Cardiovascular Monitoring, New York, Churchill Livingtosn, 1998, pp. 1-7, Jonathan B. Mark, M.D.

* cited by examiner

Primary Examiner — Mark W Bockelman
(74) Attorney, Agent, or Firm — Jack Schwartz & Associates, PLLC

(57) ABSTRACT

An ECG system is used in ECG signal measurement of intra-cardiac ECG using a catheter. The system includes a lead signal switch for disconnecting an amplifier input terminal from a reference point and reconnecting the input terminal to a patient limb electrode. An ECG signal processor amplifies the difference of a chest lead signal electronically connected to a catheter, and a patient limb signal provided by the reconnecting of the input terminal.

20 Claims, 2 Drawing Sheets

US 8,155,732 B2

ECG SYSTEM FOR USE IN ECG SIGNAL MEASUREMENT OF INTRA-CARDIAC ECG USING A CATHETER

FIELD OF THE INVENTION

The present invention relates to system for providing ECG signals and in particular to a system which is used in conjunction with a central venous catheter and derivation of an intra-cardiac ECG signal using such a catheter.

BACKGROUND OF THE INVENTION

It is known to insert a central venous pressure catheter into a central vein near the heart of a patient. Properly locating the end of such a catheter is important. The use of an ECG electrode at the end of the catheter to assist during the insertion and proper location of such a catheter is a standard procedure. By monitoring the ECG lead signal produced by such an ECG electrode, the end of the catheter may be accurately placed in the appropriate location, while minimizing risks from improper location.

In the past, ECG leads were removed from standard positions on the patient and connected to the ECG electrode at the end of the catheter. In particular, the right arm (RA) lead was often used for this purpose. But using this lead for inserting and locating the catheter impaired the derivation of the Einthoven ECG lead signals because the RA lead is now located in the central vein location and not on the right arm. Further, various other alarms and other calculations (arrhythmia detection, ST measurement, etc.) are distorted.

Further, in normal ECG operation, one limb signal (e.g. the right leg RL signal) is used to provide a reference potential (neutral or ground), and the remaining are coupled to a reference point (termed the Wilson Star point) through respective impedances. This reference point is coupled in common to respective input terminals of a plurality of differential amplifiers. Chest electrodes (e.g. V1, V2, V3, V4, V5, V6) are coupled to respective second input terminals of the plurality of differential amplifiers. The signals from the differential amplifiers are processed to generate ECG chest lead signals. The ECG chest lead signals are displayed by being printed out on a chart recorder and/or displayed on a display device.

However, the intra-cardiac ECG lead signal is the difference between the signal from the ECG electrode at the end of the catheter and a limb signal, typically the left leg LL signal. This requires a re-wiring of the ECG signal processor, or produces a distorted intra-cardiac ECG lead signal.

A system which permits a chest lead electrode conductor to be connected to an ECG electrode at the end of a central venous catheter, which produces an accurate intra-cardiac ECG signal, and which does not require moving of the other ECG electrodes already applied to the patient is desirable.

BRIEF SUMMARY OF THE INVENTION

In accordance with principles of the present invention, an ECG system is used in ECG signal measurement of intra-cardiac ECG using a catheter. The system includes a lead signal switch for disconnecting an amplifier input terminal from a reference point and reconnecting the input terminal to a patient limb electrode. An ECG signal processor amplifies the difference of a chest lead signal electronically connected to a catheter ECG electrode, and a patient limb signal provided by the reconnecting of the input terminal.

DETAILED DESCRIPTION OF THE INVENTION

Figure 1:
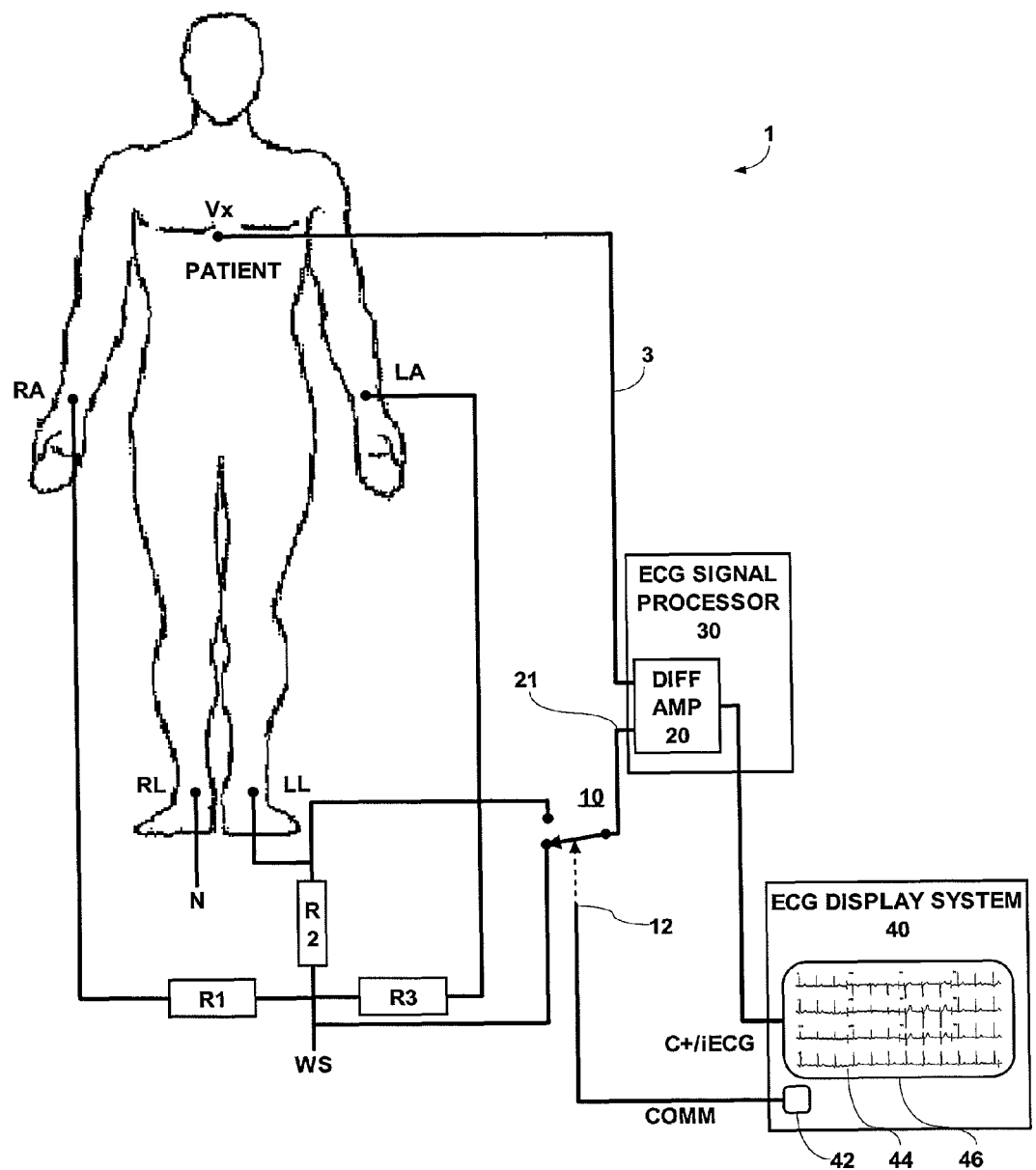
FIG. 1 and FIG. 2 are diagrams, partially in schematic form, and partially in block diagram form, illustrating an ECG system for use in ECG signal measurement of intra-cardiac ECG using a catheter, in accordance with principles of the present invention.
Figure 2:
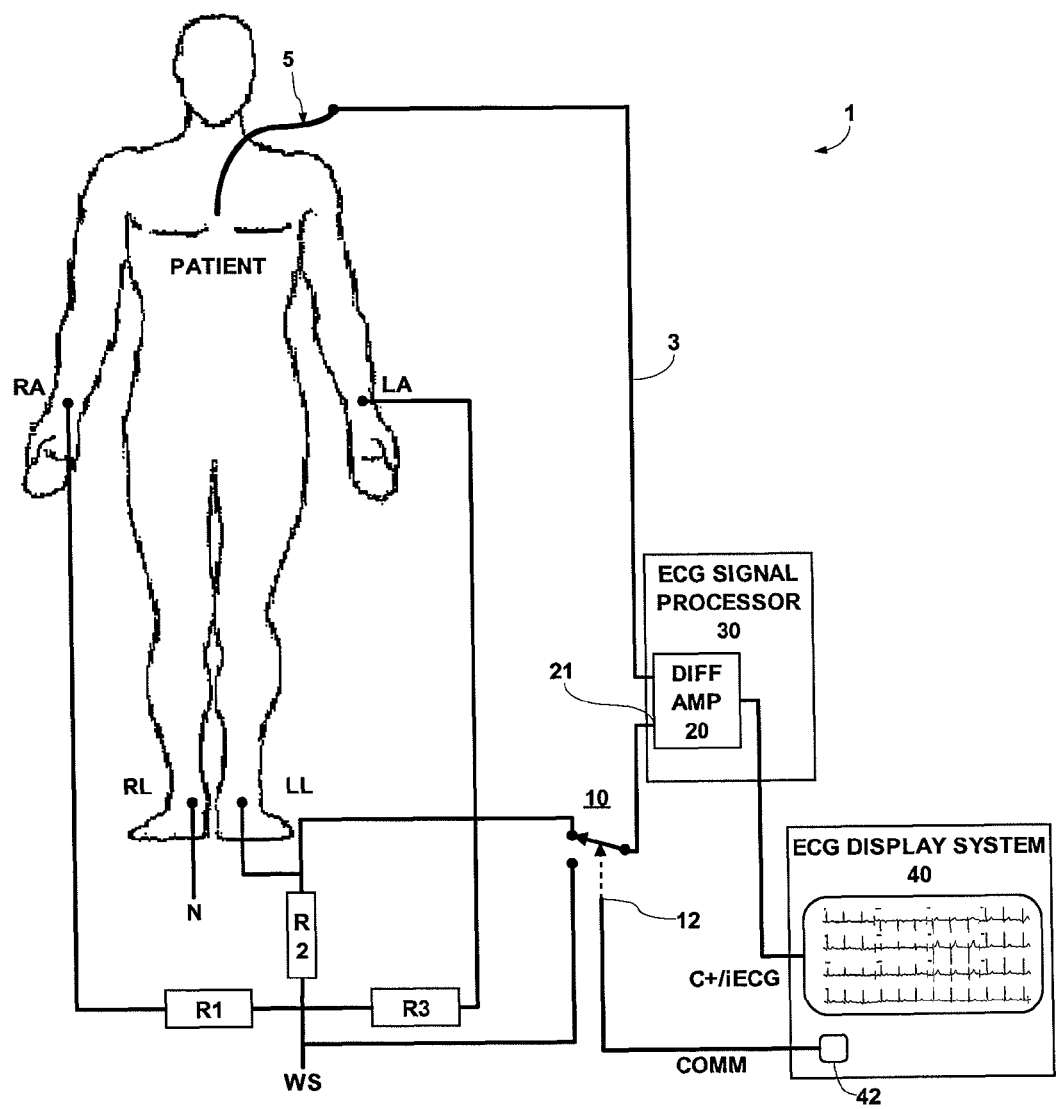

FIG. 1 and FIG. 2 illustrate an ECG system 1 for use in ECG signal measurement of intra-cardiac ECG using a catheter, in accordance with principles of the present invention. In FIG. 1, the system 1 is configured to provide a standard ECG of a patient and in FIG. 2 the system 1 is configured to provide an intra-cardiac ECG using a catheter 5. Referring concurrently to FIG. 1 and FIG. 2, a lead signal switch 10 disconnects an amplifier 20 input terminal 21 from a reference point WS (FIG. 1) and reconnects the input terminal 21 to a patient limb electrode, e.g. a left leg LL electrode (FIG. 2). The reference point WS may be the Wilson Star point. The lead signal switch 10 may be implemented in (a) hardware and/or (b) software. In addition, the lead signal switch 10 may operate in response to a user command COMM entered via an ECG signal display system 40 user interface 42. An ECG signal processor 30 amplifies 20 the difference of a chest lead signal connected to a catheter 5 (FIG. 2) and a patient limb (e.g. left leg) signal provided by reconnecting the input terminal 21. In an embodiment, the chest lead signal conductor 3 electronically connected to the catheter 5 is an unused chest lead signal conductor. More specifically, the chest lead electrode is one of a V1, V2, V3, V4, V5 or V6 signal electrode of a conventional 12 lead ECG signal set. The lead signal switch 10 reconnects the input terminal 21 of the amplifier 20 to the patient left leg electrode LL without impairing the derivation of the Einthoven signals derived from the other ECG electrodes (e.g. V1, V2, V3, V4, V4, V6).

Referring to FIG. 1, electrodes are applied to the patient in the typical manner. Four limb electrodes are applied to appropriate locations on the patient right arm (RA), left arm (LA), right leg (RL) and left leg (LL). During normal ECG operation, as illustrated in FIG. 1, the right leg RL electrode provides a reference potential (neutral (N) or ground). The right arm RA, left leg LL, and left arm LA limb electrodes are coupled to a reference point, sometimes termed the Wilson Star (WS) point, through impedances R1, R2 and R3 respectively. In addition, a plurality of chest electrodes (e.g. V1 to V6) are applied to predetermined standard locations on the patient's chest. In FIG. 1 only a single chest electrode, designated Vx is illustrated to simplify the figure. One skilled in the art understands that other chest electrodes may be concurrently applied to the patient and where they are applied. One skilled in the art further understands that the respective chest leads (e.g. V1, V2, V3, V4, V5, V6) are coupled to respective first input terminals of corresponding differential amplifiers (e.g. 20), and that the reference point (e.g. WS point) is coupled in common to respective second input terminals of the corresponding differential amplifiers (e.g. 20). The output terminals of the respective differential amplifiers provide ECG chest lead representative signals C+ and are coupled to the ECG display system 40 where those signals are processed to produce image representative signals for displaying the respective ECG chest lead signals 44 on a display device 46. Such processing is known, is not germane to the present invention and consequently is not described in detail.

Referring to FIG. 2, a central venous catheter (CVC) 5 is shown inserted into the patient ending in the Vena Cava near the heart of the patient. The process for inserting the catheter 5 and verifying proper placement uses an ECG lead signal generated by an electrode located at the end of the catheter 5. The catheter 5 is filled with saline solution and consequently acts as a conductor. The ECG electrode at the end of the catheter is electrically connected to the ECG signal processor 30 via the saline solution in the catheter 5, and the chest lead conductor 3, to provide an intra-cardiac ECG (iECG). To provide the iECG lead representative signal, the differential amplifier 20 is reconfigured by the lead signal switch 10. The Vx chest lead conductor 3 is connected to the ECG electrode via the saline solution in the catheter 5. Concurrently, the other input terminal of the differential amplifier 20 is connected to the left leg LL electrode through the lead signal switch 10. In this configuration, the differential amplifier 20 produces a signal representing the iECG lead signal. This signal is supplied to the ECG display system 40 where that signal is processed to produce an image representative signal displaying the iECG lead signal 44 on the display device 46.

One skilled in the art recognizes that other embodiments may not employ saline solution in the catheter 5 as a conductor, but alternatively, for example, may employ a guide wire in the catheter as a conductor.

The ECG display system 40 includes a user interface which may accept user commands. In FIG. 1 and FIG. 2, the user interface is represented by a button 42. The button 42 is coupled to a control terminal 12 of the lead signal switch 10. The command signal COMM from the button 42 controls the position of the lead signal switch 10. One skilled in the art understands that the user interface may include a series of buttons aligned alongside the display device 46 with labels displayed on the display device 46 giving the function of those buttons. Or the display device 46 may be a touch screen with virtual buttons outlined on the screen which are activated by touching those buttons. Or the buttons may be mechanical buttons, switches, knobs, or other similar devices capable of generating a user command signal COMM for controlling the state of the lead signal switch 10. Such a user interface 42 permits a user to designate any unused chest electrode conductor (e.g. 3) to connect to ECG electrode at the end of the catheter 5 by controlling the lead signal switch 10 associated with the particular amplifier 20 associated with that chest electrode conductor 3.

Because there are clinical situations, such as chest surgery, where the standard locations for some of the chest electrodes (V1, V2, V3, V4, V5, V6) are unavailable for use, there are often unused chest electrode conductors (e.g. 3). In such situations, the unused chest electrode conductor (e.g. 3) may be used to connect to the CVC catheter 5. Further, by reconnecting the amplifier 20 input terminal 21 as described above using the lead signal switch 10, the ECG electrodes applied to the patient and the associated conductors coupled between the electrodes and the associated amplifiers (e.g. 20) need not be moved. In particular, in the case of limb electrodes RA, RL, LL, LA, moving these electrodes interferes with the derivation of the Einthoven lead signals, which depend on the placement of the electrodes in standard predetermined locations on the patient. The system 1 described above allows these electrodes to remain in the standard locations, and does not impair the derivation of the Einthoven lead signals.

The system 1 was described above, and illustrated in FIG. 1 and FIG. 2, in terms of analog circuitry: i.e. switch 10 and differential amplifier 20. One skilled in the art understands that the implementation details of these components is not germane. These components may be implemented in hardware or software, in semiconductor form or mechanical form, or any other form which provides the similar capabilities. One skilled in the art understands the alternatives available, how to decide among them, and how to implement them to provide the capabilities described above.

For example, an embodiment of the system may algorithmically "disconnect" from the reference point WS and algorithmically "connect" the electrode to the left leg. This "disconnect" and "reconnect" may be accomplished by processing the lead signal through circuitry or software to provide an actual or calculated equivalent waveform.

Although the invention has been described in terms of exemplary embodiments, it is not limited thereto. Rather, the appended claims should be construed broadly to include other variants and embodiments of the invention which may be made by those skilled in the art without departing from the scope and range of equivalents of the invention. This disclosure is intended to cover any adaptations or variations of the embodiments discussed herein.

What is claimed is:

1. An ECG system for use in ECG signal measurement of intra-cardiac ECG using a catheter, comprising:
an external lead configuration having at least two limb electrodes with a common node connection reference point therebetween and at least a left leg electrode lead connection point,
a lead signal switch for disconnecting a first input terminal of an amplifier from the common node connection reference point and reconnecting said input terminal to said left leg electrode lead connection point; and
an ECG signal processor including said amplifier having said first input terminal and a second input terminal, said second input terminal being electrically connected to a catheter ECG electrode via a chest lead signal conductor for amplifying the difference of:
a chest lead signal sensed by the catheter ECG electrode, and
a patient limb signal provided by said reconnecting said input terminal.

2. The system of claim 1 wherein said chest lead signal electronically connected to said catheter ECG electrode is an unused chest lead signal.

3. The system of claim 1 wherein said chest lead signal electrode comprises a V1, V2, V3, V4, V5 or V6 signal electrode of a conventional 12 lead ECG signal set.

4. The system of claim 1 wherein said lead signal switch is implemented in at least one of, (a) hardware and (b) software.

5. The system of claim 1 wherein the reference point is the Wilson Star point.

6. The system of claim 1 wherein the lead signal switch reconnects the input terminal of the amplifier to the patient limb electrode without impairing the derivation of the Einthoven signals.

7. The system of claim 1 wherein the lead signal switch reconnects the input terminal of the amplifier to the patient limb electrode while maintaining the connections of other electrodes connected to said reference point.

8. An ECG system for use in ECG signal measurement of intra-cardiac ECG using a catheter, comprising:
an external lead configuration having at least two limb electrodes with a common node connection reference point therebetween and at least two limb lead electrode connection points,
a lead signal switch for disconnecting a first input terminal of an amplifier from a common node connection reference point and re-connecting said input terminal to one of said at least two limb lead electrode connection points in response to a user command entered via an ECG signal display system user interface without impairing the signals of other electrodes connected to said common node connection reference point; and an ECG signal processor including said amplifier having said first input terminal and a second input terminal being electrically connected to a catheter ECG electrode via a chest lead signal conductor for amplifying the difference of, a chest lead signal sensed by the catheter ECG electrode, and a patient limb signal provided by said re-connecting said input terminal.

9. The system of claim 8 wherein the lead signal switch reconnects the input terminal of the amplifier to the patient limb electrode without impairing the connections of other electrodes connected to said reference point.

10. The system of claim 8 wherein said chest lead signal electronically connected to said catheter ECG electrode is an unused chest lead signal.

11. The system of claim 8 wherein said chest lead signal electrode comprises a V1, V2, V3, V4, V5 or V6 signal electrode of a conventional 12 lead ECG signal set.

12. The system of claim 8 wherein the reference point is the Wilson Star point.

13. The system of claim 8 wherein the lead signal switch reconnects the input terminal of the amplifier to the patient limb electrode without impairing the derivation of the Einthoven signals.

14. An ECG system for use in ECG signal measurement of intra-cardiac ECG using a catheter, comprising:

an external lead configuration having at least two limb electrodes with a common node connection reference point therebetween and at least two limb lead electrode connection points, a lead signal switch for disconnecting a first input terminal of an amplifier from the common node connection reference point and re-connecting said input terminal to one of the at least two limb lead electrode connection points while maintaining connections of other electrodes connected to said reference point; and an ECG signal processor having a first input connected to the lead signal switch and a second input electrically connected to a catheter ECG electrode via a chest lead signal conductor for amplifying the difference of, a chest lead signal sensed by the catheter ECG electrode, and a patient limb signal provided by said re-connecting said input terminal.

15. The system of claim 14 wherein the lead signal switch reconnects the input terminal of the amplifier to the patient limb electrode while maintaining the connections of other electrodes connected to said reference point.

16. The system of claim 14 wherein said chest lead signal electronically connected to said catheter ECG electrode is an unused chest lead signal.

17. The system of claim 14 wherein said chest lead signal electrode comprises a V1, V2, V3, V4, V5 or V6 signal electrode of a conventional 12 lead ECG signal set.

18. The system of claim 14 wherein the reference point is the Wilson Star point.

19. The system of claim 14 wherein the lead signal switch reconnects the input terminal of the amplifier to the patient limb electrode without impairing the derivation of the Einthoven signals.

20. The system of claim 14 wherein the one of the at least two limb lead electrode connection points is the patient left leg electrode connection points.

* * * * *